United States Patent
Ergun et al.

(10) Patent No.: US 9,655,376 B2
(45) Date of Patent: *May 23, 2017

(54) PROCESS FOR PREPARING AN OLEOGEL

(71) Applicant: Dow Global Technologies LLC, Midland, MI (US)

(72) Inventors: Roja Ergun, Midland, MI (US); Robert B. Appell, Midland, MI (US); David L. Malotky, Midland, MI (US)

(73) Assignee: Dow Global Technologies LLC

( * ) Notice: Subject to any disclaimer, the term of this patent is extended or adjusted under 35 U.S.C. 154(b) by 13 days.

This patent is subject to a terminal disclaimer.

(21) Appl. No.: 14/892,354

(22) PCT Filed: May 16, 2014

(86) PCT No.: PCT/US2014/038383
§ 371 (c)(1),
(2) Date: Nov. 19, 2015

(87) PCT Pub. No.: WO2014/193667
PCT Pub. Date: Dec. 4, 2014

(65) Prior Publication Data
US 2016/0081374 A1    Mar. 24, 2016

Related U.S. Application Data

(60) Provisional application No. 61/829,582, filed on May 31, 2013.

(51) Int. Cl.
| | | |
|---|---|---|
| A23L 1/06 | (2006.01) |
| A23L 1/0534 | (2006.01) |
| A23D 9/007 | (2006.01) |
| A23D 9/02 | (2006.01) |
| A61K 8/73 | (2006.01) |
| A23D 7/005 | (2006.01) |
| A61K 8/37 | (2006.01) |
| A61Q 19/00 | (2006.01) |
| A61K 8/92 | (2006.01) |
| A61K 8/04 | (2006.01) |
| A61K 47/38 | (2006.01) |
| A61K 47/44 | (2017.01) |
| A23D 9/04 | (2006.01) |
| A61K 9/06 | (2006.01) |
| A23L 29/262 | (2016.01) |

(52) U.S. Cl.
CPC .......... *A23L 1/0534* (2013.01); *A23D 7/0056* (2013.01); *A23D 9/007* (2013.01); *A23D 9/02* (2013.01); *A23D 9/04* (2013.01); *A23L 29/262* (2016.08); *A61K 8/042* (2013.01); *A61K 8/37* (2013.01); *A61K 8/731* (2013.01); *A61K 8/922* (2013.01); *A61K 9/06* (2013.01); *A61K 47/38* (2013.01); *A61K 47/44* (2013.01); *A61Q 19/00* (2013.01); *A23V 2002/00* (2013.01); *A61K 2800/10* (2013.01); *A61K 2800/592* (2013.01); *A61K 2800/92* (2013.01)

(58) Field of Classification Search
USPC ................................................. 426/574, 573
See application file for complete search history.

(56) References Cited

U.S. PATENT DOCUMENTS

| | | | |
|---|---|---|---|
| 2012/0064219 A1 | 3/2012 | Barra et al. | |
| 2015/0157038 A1* | 6/2015 | Ergun | ................... A23L 1/0534 426/573 |

FOREIGN PATENT DOCUMENTS

WO    2011159653 A1    12/2011

OTHER PUBLICATIONS

Gravelle et al., Ethylcellulose oleogels: Manufacturing considerations and effects of oil oxidation, Food Research International, vol. 48, 2012, pp. 578-583.

* cited by examiner

*Primary Examiner* — Rei-Tsang Shiao

(57) ABSTRACT

A continuous process for preparing an oleogel from ethylcellulose and an oily feed material, wherein the process comprises: (a) feeding ethylcellulose to the feed zone of an extruder, the extruder having a plurality of oil feed ports along its length; (b) feeding at least one oily feed material into at least one of the oil feed ports; (c) mixing the oily feed material with the ethylcellulose to form a substantially homogeneous mixture; (d) cooling the mixture to form an oleogel.

12 Claims, 1 Drawing Sheet

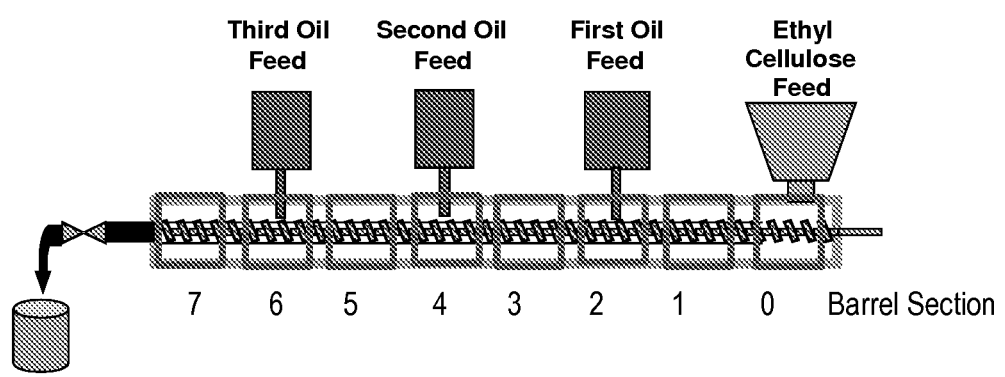

PROCESS FOR PREPARING AN OLEOGEL

CROSS-REFERENCE TO RELATED APPLICATIONS

This application claims priority from provisional application Ser. No. 61/829,582, filed May 31, 2013, which is incorporated herein by reference in its entirety.

BACKGROUND OF THE INVENTION

The present invention relates to a process for preparing an oleogel.

Structure in solid fat-containing food products is provided by the network of crystalline triacylglycerols. However, these triacylglycerols contain high levels of saturated fatty acids. Instead of using naturally highly saturated solid fats, oils comprising triacylglycerols having high levels of unsaturated fatty acids are also transformed to more solid products by hydrogenation or partial hydrogenation. "Trans fats", which are unsaturated fats with trans-isomer, unavoidably emerge from partial hydrogenation of unsaturated oils. Research into the role fats and oils play in human health has indicated that consumption of saturated fatty acids, especially trans fatty acids, is associated with elevated cholesterol levels and cardiovascular diseases.

Therefore, it would be desirable to develop healthier alternatives to triacylglycerols containing saturated or partially hydrogenated fatty acids. The demand for a healthy alternative to trans fats and saturated fats creates technological hurdles for the food manufacturing industry. It is difficult to eliminate trans and saturated fats from a food formulation where the goal is to transform a healthier unsaturated oil, which is liquid at room temperature, to a fat, which is 'solid' at room temperature, in order to enhance the texture and appearance of a food product.

In the food industry there have been many attempts to find alternative components that can provide the desired features of texture, structuring, stability and taste that are normally found in animal and vegetable fats or hydrogenated oils. One alternative, organogels (oleogels), have been recognized for their potential to be used to reduce oil migration in multi-component foods and to act as an alternative to butter or margarine. Oleogels can be used to provide structure to edible oils thereby reducing the need for saturated and trans fatty acids.

An ethylcellulose oleogel may also be useful as an ingredient to a cosmetic composition to render a film left by the composition more hydrophobic and resistant to rub off. An ethylcellulose oleogel may also be the carrier phase of a cosmetic or cosmeceutical product. The ethylcellulose oleogel could also be used to deliver an active in a cosmetic or cosmeceutical product.

U.S. Pat. No. 6,187,323 describes the preparation under non-shear conditions of pharmaceutical and cosmetic compositions comprising a mixture of an oleogel and an aqueous gel. In the example, a semisynthetic triglyceride is gelled with ethylcellulose in the presence of propylene glycol isostearate by stirring the components at 140° C. until a uniform oleogel is formed.

In "Influence of the Concentration of a Gelling Agent and the Types of Surfactant on the Rheological Characteristics of Oleogel" (Il farmaco 58 (2003) 1289-1294) M. A. RuíMartínez et al. report on oleogels comprising olive oil, ethylcellulose and a surfactant selected from Olivem 300, 700 and 900. The oleogels were prepared by adding ethylcellulose and a surfactant to the oil phase, then stirring the components while heating to 100° C.

U.S. Pat. No. 4,098,913 describes edible fat particles for incorporation into textured protein meat analog products. The edible fat products are made by gelling a triacylglyceride fat or oil with ethylcellulose. In the example, partially hydrogenated cottonseed oil is mixed under rapid stirring with ethylcellulose at 180° C.

WO 2010/143066 relates to an edible oleogel comprising an oil, ethylcellulose and a surfactant. The oleogel is obtained by heating the ethylcellulose and the surfactant in oil to a temperature (Tg) above the glass transition temperature of the ethylcellulose with constant mixing. Suitably, the mixture is heated up to at least 130° C. to about 160° C. and after a few minutes a clear and very viscous solution is formed.

The problem underlying the present invention is to provide a new process of preparing a solid or semi-solid fat product, such as an oleogel.

SUMMARY OF THE INVENTION

The invention is such a process comprising:
(a) feeding ethylcellulose to the feed zone of an extruder, the extruder having a plurality of oil feed ports along its length;
(b) feeding at least one oily feed material into at least one of the oil feed ports;
(c) mixing the oily feed material with the ethylcellulose to form a substantially homogeneous mixture;
(d) cooling the mixture to form an oleogel.

Surprisingly, the process of the invention can provide an oleogel that is superior to those of the art.

The oleogel of the invention may be used in culinary, pharmaceutical, veterinary and cosmetic applications, depending on the ingredients used in its preparation. For example, the process of the invention is capable of creating oleogels of ethylcellulose gelled with oil that could serve as a healthy alternative to solid fats in food without sacrificing functionality or mouth feel.

BRIEF DESCRIPTION OF THE DRAWINGS

FIG. 1 is a schematic of the extruder process used to create oleogels in Example 1.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The process of the invention employs an oily feed material and ethylcellulose.

The oily feed material can be a natural, synthetic or semi-synthetic oil or fat, or a mixture thereof. In one embodiment of the invention, the oily feed material is a triacylglycerol oil or fat. In preferred embodiments it is a fat or oil of natural origin such as a vegetable or animal oil or vegetable or animal fat; typically the triacylglycerol is a vegetable oil or fat. MIGLYOL 810 AND 812, and LABRAFIL M 1944 CS are examples of synthetic and semi-synthetic triglycerides, respectively.

In one embodiment of the invention, the triacylglycerol oil or fat is edible. The term "triacylglycerol oil" designates triacylglycerols that are liquid at 20° C. and atmospheric pressure (1013.25 hPa) whereas the term "triacylglycerol fat" designates triacylglycerols that are solid or semi-solid at 20° C. and atmospheric pressure (1013.25 hPa). The liquid nature of triacylglycerol oils is due to their higher content of healthier mono- or polyunsaturated fatty acids that prevent an arrangement in a crystalline structure. The oleogel of the invention preferably contains triacylglycerol oil(s). In preferred embodiments the triacylglycerol(s) oils or fats have a iodine value of at least 30, more preferably of at least 70 and in certain embodiments of at least 80. The iodine value is determined according to method AOCS Official Method Cd 1-25 (Wijs method).

Exemplary triacylglycerol oils that can be employed in the oleogel include canola oil, sunflower oil, corn oil, flaxseed oil, olive oil, soybean oil, safflower oil, peanut oil, grape seed oil, sesame oil, argan oil, rice bran oil, algal oil and echium oil. Exemplary triacylglycerol fats for use in the present invention are cocoa butter and palm oil. Examples of animal oils include squid oil and fish oils such as salmon oil and halibut oil. Mixtures of various triacylglycerol oils and fats (including mixtures of at least two different oils, mixtures of at least two different fats and mixtures of at least one oil and at least one fat) as well as fractions and mixtures of fractions of triacylglycerol oils and fats can also be employed. In more preferred embodiments the oleogel contains at least one of canola oil, olive oil, palm oil, cocoa butter, flaxseed oil and sunflower oil.

Preferably, the ethylcellulose for use in the present invention has a degree of substitution (DS) of from 2 to 3, preferably from 2.42 to 2.80, more preferably from 2.43 to 2.70, even more preferably from 2.44 to 2.65, still more preferably from 2.45 to 2.60, and most preferably from 2.46 to 2.57. In typical embodiments, the ethylcellulose, including ethylcellulose having the preferred DS described before, has a 5% solution viscosity of from 3 to 110 mPa·s, preferably from 16 to 76 mPa·s, and more preferably from 18 to 50 mPa·s. The term "5% solution viscosity" refers to the viscosity of a 5 weight percent solution of the ethylcellulose measured at 25° C. in a mixture of 80 volume percent toluene and 20 volume percent ethanol. The ethylcellulose concentration is based on the total weight of toluene, ethanol and ethylcellulose. The viscosity is measured using Ubbelohde tubes as outlined in ASTM D914-00 and as further described in ASTM D446-04, which is referenced in ASTM D914-00.

A typical viscosity analysis is performed as follows: 57 g of an 80/20 w/w toluene/ethanol mixture are weighed into a dry 8-ounce bottle and 3 g (dry weight) of ethylcellulose are added. The bottle is placed on a mechanical shaker and shaken until all material goes into solution (approximately 20 min). The resulting solution is analyzed within 24 h of preparation. For viscosity measurement, the solution is filled in a Ubbelohde viscometer that is then placed in a water bath at 25° C. until the solution has equilibrated to 25° C. Following the instructions for the Ubbelohde viscometer, the solution is sucked up through the calibration flow tube and then allowed to drain. The viscosity is calculated based on the time it takes for the solution to flow between the upper and lower calibration mark according to the instructions taking into account the specific capillary used for the measurement. The values of the 5% solution viscosities reflect the molecular weight of the ethylcellulose.

Exemplary ethylcelluloses that can be used in the process of the present invention include ETHOCEL™ Std. 4, ETHOCEL™ Std. 7, ETHOCEL™ Std. 10, ETHOCEL™ Std. 14, ETHOCEL™ Std. 20, and ETHOCEL™ Std. 45, which are all commercially available from The Dow Chemical Company, Midland, U.S.A. ETHOCEL™ Std. 20 (DS=2.46 to 2.57, 5% solution viscosity=18-22 mPa·s) and ETHOCEL™ Std. 45 (DS=2.46 to 2.57, 5% solution viscosity=41-49 mPa·s) are most preferred. Combinations of the exemplary ethylcelluloses can also be used. The level of gelling provided by the ethylcellulose in the oleogel is a function of the proportion of ethylcellulose employed as well as the grade of the ethylcellulose, as is known to those skilled in the art.

The oily feed material and ethylcellulose are employed in a weight ratio of from 99:1 to 75:25, preferably from 95:5 to 85:15, more preferably from 92:8 to 87:13, and most preferably in a weight ratio of about 90:10.

Typically, the oleogel comprises from 70 to 99% by weight, preferably from 75 to 95% by weight, more preferably from 80 to 92% by weight and most preferably from 85 to 90% by weight of the oily feed material.

In the inventive process, the oily feed material and the ethylcellulose are fed to an extruder. The extrusion is advantageously conducted under a set of process conditions that provide an oleogel product that has a smooth, substantially homogeneous texture.

In one embodiment of the invention, the ethylcellulose is fed to the back end atmospheric add port of the extruder, and the oily feed material is fed into one or more input ports located along the length of the extruder. In one embodiment of the invention, the ethylcellulose is fed to the extruder alone at the ethylcellulose feed point. In various embodiments of the invention, the oily feed material is fed to at least 2 different input ports, at least 3 ports, at least 5 ports, or 6 or more ports. In one embodiment of the invention, the first feed port for the oily feed material is located at a point on the extruder where the ethylcellulose has at least partially, and preferably has fully, melted.

The total oily feed material added to the system is preferentially added in a number of steps in the extruder to gradually reduce the concentration of the ethylcellulose in the composition and to avoid large amounts of unincorporated liquid that may cause slip and poor mixing between the oily feed material and the ethylcellulose melt.

Advantageously, the ethylcellulose is subjected to time and temperature conditions in the extruder sufficient to melt the ethylcellulose and/or raise its temperature above the Tg of the ethylcellulose. In addition, the materials in the extruder are subjected to time and temperature conditions sufficient to produce an oleogel, preferably a substantially homogeneous oleogel that is smooth and free from grainy/sandy texture.

The temperature within the extruder advantageously varies along the length of the extruder. In one embodiment of the invention, the extruder is set up to provide an ethylcellulose feed zone, an ethylcellulose softening zone, a melting zone, and a cooling zone. The temperature may vary between the zones and may vary even in a zone. As ethylcellulose enters the extruder in the feed zone, no additional heat is required, and preferably no additional heat is supplied. The temperature in the softening zone is relatively low in order to soften the ethylcellulose. As the ethylcellulose proceeds down the length of the extruder, higher temperatures are employed in the melting zone in order to melt the ethylcellulose and provide good mixing of the ethylcellulose and the oil. The majority of the oil, up to 100%, is added in the melting zone. The temperature in the cooling zone is advantageously lower than that of the melting zone, and lowers the temperature of the mixture before it leaves the extruder.

Advantageously, the temperature in the feed zone is around ambient temperature such as, for example, from 15 to 75° C. The temperature in the softening zone advantageously is from 25 to 130° C., preferably from 75 to 130° C. The temperature in the melting zone advantageously is from 100 to 200° C., preferably 130 to 180° C. As is known to those skilled in the art, the Tg of ethylcellulose can be lowered by the addition of a plasticizer. The temperature in the cooling zone advantageously is from 90 to 160° C. Advantageously, the temperature is at least 135° C. in zones in which oil is added.

Generally speaking, it is advantageous to minimize the heat history of the mixture in the extruder in order to reduce the overall level of oxidation of the resulting oleogel. For example, a lower peak temperature in the melting zone may result in lower oleogel oxidation levels.

It is known to the person skilled in the art that higher temperatures require only short holding times whereas lower temperatures require longer holding times. The specific temperature and residence time required depend on the type of ethylcellulose (e.g., its molecular weight) and the type of oil or fat, and the actual residence time in the continuous process depends upon the feed rates of the oleogel ingredients to the extruder. In some embodiments, the oleogel ingredients are heated and passed through the extruder under shear conditions wherein the temperature in the melting zone is from 130 to 200° C. for less than 1 up to 10 min, such as at a temperature of from 145 to 160° C. for 1 to 5 min. The stage of solubilization of the ethylcellulose in the triacylglycerol oil/fat in the oleogel is typically determined by feel with hand inspection. If the resulting oleogel has a grainy/sandy texture at 23° C. then the ethylcellulose is not fully soluble. If the oleogel gel has a smooth texture at 23° C. then the ethylcellulose is considered to be soluble at the processing temperature.

The extruder can be configured such that it has various temperature control means, as is well known to those skilled in the art. Examples of temperature control measures include, for example, temperatures of the feed streams, jacket and/or shaft heating or cooling, and evaporative cooling under reduced pressure. The extruder can have multiple temperature control zones.

Any melt-kneading means and equipment known in the art may be used. In some embodiments a single-screw extruder, or a multi-screw extruder, e.g., a twin screw extruder, is used. The process for producing the ethylcellulose oleogel in accordance with the present invention is not particularly limited. For example, an extruder, in certain embodiments, for example, a twin screw extruder, is coupled to a back pressure regulator, melt pump, or gear pump at the extruder outlet to maintain fill of the oleogel in the extruder. Exemplary embodiments also provide a reservoir for the oil and a number of oil pumps equal to the number of oil injection locations along the extruder length. Any suitable pump may be used, but in some embodiments, for example, a pump that provides a flow of about 150 cc/min at a pressure of 240 bar is used to provide the first, second, and third oil additions. In other embodiments, the liquid injection pumps provide a flow of 300 cc/min at 200 bar or 600 cc/min at 133 bar. In some embodiments, the liquid oil feeds are preheated in a preheater. The oil flow rates will vary to some extent based on the size of the extruder and the residence time.

One or more ethylcellulose grades, in the form of pellets, powder, or flakes, are fed from the feeder to an inlet of the extruder where the resin is melted or compounded. The resin melt is then delivered from the melt and convey zone to a liquid mix zone where the first addition of oil is added through an inlet. In some embodiments, the oil may be a blend of components. In some embodiments, further oil addition occurs later down the barrel at second and third oil addition zones. Oil and other liquid ingredients may be added to the ethylcellulose melt any number of times until the desired concentration of oleogel is achieved. In some embodiments, not all of the oil is added while the oleogel is in the twin screw extruder, but rather to a stream containing the more concentrated oleogel after this concentrated oleogel has exited from the extruder. In this manner, a more efficient liquid—liquid mixing device such as a rotor stator mixer may be used to form the final oleogel.

The process of the invention can be conducted under an inert atmosphere at the extruder inlet and outlet, such as under an inert gas atmosphere, or in ambient air. In one embodiment of the invention, the process is operated in a manner such that essentially no oxygen is in the barrel of the extruder. Advantageously, the use of an inert or reduced oxygen atmosphere in the extruder may reduce the oxidation levels in the final oleogel. Examples of inert gases that may be used according to the present invention include nitrogen and noble gases such as, for example, argon. It is preferred to conduct the process in the extruder under a nitrogen gas atmosphere due to the inert nature, ready availability and relatively low cost of nitrogen gas. Processing under an inert atmosphere is applied to reduce, preferably minimize, and most preferably substantially exclude, the presence of oxygen. However, in practice, the inert atmosphere may still contain minor amounts of oxygen.

Any technique to create an inert gas atmosphere may be applied in the present invention, including continuously purging the system containing the mixture of triacylglycerol oil or fat and ethylcellulose with an inert gas such as nitrogen, e.g., with a continuous gas flow, in order to drive out air and ensure that air is not reintroduced into the system. It is also possible evacuate the system to remove the air before the inert gas is introduced into the system.

The mixture that exits the extruder is cooled, actively, passively, or both. For example, the mixture may be collected and allowed to cool to a desired temperature, or it may be actively cooled as it leaves the extruder, e.g., by contacting the mixture with a cooling bath, or a cooled surface. In one embodiment, the mixture is passively cooled, e.g., allowed to cool, typically to ambient temperature, for example to a temperature of less than 30° C. or to a temperature equal to or less than 25° C. or to a temperature of equal to or less than 23° C. or to a temperature of equal to or less than 20° C. It is preferred that the cooling is conducted under an inert atmosphere such as under a nitrogen atmosphere. In preferred embodiments the inert gas purge, i.e., the inert gas flow through the system, is continued during cooling.

When ethylcellulose is heated above its glass transition temperature, the ethylcellulose is solubilized in the oil or fat to create a three-dimensional, thermo-reversible gel network upon cooling. Due to the restricted mobility and migration of the oil/fat inside the polymer network, the oleogels produced by the process of the invention provide the solid-like properties of crystalline triacylglycerols without the high levels of saturated fatty acids. Replacing saturated triacylglycerols with healthy oils/fats while retaining structural properties of crystalline/solid fats is highly desirable for various food applications.

In one embodiment of the invention, an ethylcellulose melt is directly mixed with the liquid oil, preferentially in multiple stages so there is efficient transfer of mixing energy to the viscous ethylcellulose melt that allows the melt to quickly incorporate the oil. In the prior art, the mixing is not able to efficiently transfer energy to the viscous ethylcellulose in the oil droplets, which keeps ethylcellulose from quickly becoming incorporated into the oil.

Although a stabilizer is not necessary to prepare the oleogel, it may be added in certain embodiments to modify the properties of the oleogel, such as to increase its firmness. The stabilizer can be one that is either suitable or not suitable for use in the preparation of food, depending on the desired end use of the oleogel. Examples of stabilizers that may be used in the present process are food grade surfactants and emulsifiers such as polyoxyethylene sorbitan monooleate (Tween 80 or Polysorbate 80); polyoxyethylene sorbitan tristearate (Tween 65 or Polysorbate 65); polyoxyethylene sorbitan monostearate (Tween 60 or Polysorbate 60); sorbitan monooleate (SMO or Span 80); sorbitan monostearate (SMS or Span 60); glyceryl monooleate (GMO); glyceryl monostearate (GMS); glyceryl monopalmitate (GMP); polyglycerol esters such as polyglyceryl ester of lauric acid-polyglyceryl polylaurate (PGPL), polyglyceryl ester of stearic acid-polyglyeryl polystearate (PGPS), polyglyceryl ester of oleic acid-polyglyceryl polyoleate (PGPO) and polyglyceryl ester of ricinoleic acid-polyglyceryl polyricinoleate (PGPR); diglycerides; monoglycerides, such as succinylated monoglyceride, lactylated monoglyceride, acetylated monoglyceride, monoglyceride citrate, monoglyceride phosphate, stearyl monoglyceride citrate, and diacetyl-tartrate ester of monoglyceride; calcium stearoyl lactylate; sodium stearoyl lactylate; sucrose esters; lecithin; and triethyl citrate. If added, the stabilizer is preferably present in an amount resulting in a weight ratio of ethylcellulose/stabilizer of from 1:3 to 4:1, or a weight ratio of from 1:2 to 2:1.

In one embodiment, the oleogel does not contain any emulsifier or surfactant, i.e., no emulsifier or surfactant is added during preparation.

The oleogel of the present invention may contain additional optional ingredients such as antioxidants to further reduce oxidation. When the oleogel is edible, the antioxidants should be food grade; exemplary antioxidants for use herein include Butylated Hydroxyanisole (BHA), Butylated Hydroxytoluene (BHT), Tertiary Butyl Hydroquinone (TBHQ), ascorbic acid, sodium ascorbate, calcium ascorbate, β-carotene, tocopherols, chlorogenic acids, gallates and flavanols. Examples of non-food-grade antioxidants include octylated butylated diphenylamine, and tert-butylated phenol derivatives. If used, antioxidants are typically added in an amount of up to 10,000 ppm by weight, preferably within a range of from 50 to 1000 ppm by weight, and more preferably within a range of from 100 to 500 ppm by weight, based on the total amount of triacylglycerol oil(s) and fat(s).

The oleogels of the invention may be edible, e.g., if prepared using an edible oily feed material. They can be formulated into any food product requiring a structured solid-like or semi-solid like fat. Accordingly, in a further aspect, the invention provides a food product comprising an oleogel according to the invention. The food product may be made by mixing food components with an oleogel according to the invention. The mixing may be performed with the oleogel in the gelled state, or with the oleogel composition in the molten state followed by cooling.

The term "food product" herein refers to edible products suitably also containing one or more additional ingredients such as selected from carbohydrates (e.g., sugars and starches), proteins, dietary fiber, water, flavoring agents such as salt, colorants, and vitamins. Typically, the food product contains at least about 1% by weight of the oleogel, for example at least about 5% by weight, at least about 10% by weight or at least about 15% by weight of the oleogel. In some embodiments the food product contains less than 95% by weight of the oleogel, for example less than about 90% by weight of the oleogel. Examples of food products that can be prepared by using the oleogel include baked goods such as cookies and cakes; spreads such as margarine and chocolate spreads; chocolate, including "heat resistant" chocolate, and fillings.

In certain embodiments, the food product according to the present invention is a meat product. For example, a ground meat product such as hamburger, or a meat emulsion product such as bologna, mortadella, frankfurters, or other sausage products. Typically, the meat products of the invention comprise from 10 to 25% by weight of protein, from 5 to 35% by weight of fat (including oils and oleogels), and from 40 to 60% by weight of total water. Replacement of a fraction of the animal fat present in such products by oils, suitably vegetable oils, results in meat products having an unacceptably hard, chewy and/or gummy texture when cooked. However, replacement of a fraction of the animal fat by an oleogel according to the present invention has been found to result in meat products that do not exhibit these drawbacks.

SPECIFIC EMBODIMENTS OF THE INVENTION

The following examples are given to illustrate the invention and should not be construed as limiting its scope.

EXAMPLE 1

ETHOCEL™ Std. 45 with Refined Canola Oil (Various Ratios)

Omega 9 canola oil (available from Dow AgroSciences Indianapolis, Ind., USA) is employed as the canola oil. The typical triacyl composition of this omega 9 canola oil is: 7% saturated fats, 74% oleic acid, 17% linoleic acid and 2% linolenic acid.

ETHOCEL™ Std. 45 brand ethylcellulose is combined with refined canola oil at a variety of ratios in the extruder. A schematic of the process used is given in FIG. 1. The extruder is a 25 mm diameter 36 L/D twin screw extruder equipped with a volumetric solids feeder. The extruder has 8 zones. Zones 1-7, and the head flange at the discharge of the extruder, are equipped with temperature control means. Zones 2, 4 and 6 are equipped with liquid injector ports as oil feed means. The extruder is equipped with a 0 to 1,000 psig back pressure regulator, which is set at a pressure of from 50 to 150 psig at steady state extrusion conditions in order to ensure that the barrel of the extruder is full. Ethylcellulose is introduced into zone 0 via the volumetric solids feeder. The product exits the extruder from zone 7 and is collected in 500 ml insulated glass jars at a temperature of 135° C.

Ethylcellulose oleogels are made according to the following procedure. ETHOCEL™ Std. 45 is fed to the extruder. Oil is metered into the extruder through the liquid injector ports at a variety of rates as shown in Table 1 (addition rates) and Table 2 (addition locations) to create a number of different oleogels. An optional surfactant is added in one of the runs. Table 1 also shows the weight percentage of ethylcellulose after each oil addition. The extruder temperature set point for each barrel segment, or zone, during production of these oleogels is also given in Table 2.

A series of oleogels is generated using different process flow rates and temperature settings.

TABLE 2

| Extruder temperature profiles | | | |
|---|---|---|---|
| Feed Location | Barrel Section | Temp. Profile A Setpoint (° C.) | Temp Profile B Setpoint (° C.) |
| Feed throat | 0 | 25 | 25 |
|  | 1 | 50 | 50 |
| $1^{st}$ oil add | 2 | 155 | 155 |
|  | 3 | 155 | 155 |
| $2^{nd}$ oil add | 4 | 155 | 155 |
|  | 5 | 155 | 155 |
| $3^{rd}$ oil add | 6 | 155 | 135 |
|  | 7 | 155 | 125 |
|  | Head flange | 155 | 120 |

EXAMPLE 2

Processing Effect on the Oxidation Levels of the ETHOCEL™ Std. 45 Omega 9 Canola Oil Gel Samples 10.6% ETHOCEL™ St 45—omega 9 canola oil gel samples are prepared using the extrusion process, flow rates, and temperature profile of Example 1E. PV and p-Anisidine (p-AV) values of the samples are measured to determine their oxidation levels. The results are reported in Table 3.

Comparative Experiment A

Processing Effect on the Oxidation Levels of the ETHOCEL™ Std. 45 Omega 9 Canola Oil Gel Samples (not an Embodiment of the Invention)

A gel is prepared by heating a mixture comprising 10.6% ETHOCEL™ Std. 45 in omega 9 canola oil in an open glass container on a bench-top hot plate while stirring with an overhead mechanical stirrer. A long shafted stir bar fitted with a high shear radial flow impeller is used to stir the mixture at a constant rate during the heating process. The mixture is heated to 155° C. and is held at that temperature for 35 minutes. The product gel is tested and the PV and the p-AV values are reported in Table 3. p-AV values are determined using method Cd 18-90 published by the American Oil Chemist's Society (A.O.C.S.). PV values are determined using A.O.C.S. Official Method Cd 8b-90 except 0.01N sodium thiosulfate is used instead of 0.1N sodium thiosulfate as suggested in the method.

TABLE 1

| | | | | | | | | | | |
|---|---|---|---|---|---|---|---|---|---|---|
| | Extruder conditions | | | | | | | | | |
| Example | Barrel Temperature Profile | Extruder rpm | Eth. Feed Rate | Surf. | $1^{st}$ Oil Add | Post 1st Eth. (wt %) | $2^{nd}$ Oil Add | Post 2nd Eth. (wt %) | $3^{rd}$ Oil Add | Final Eth. (wt %) |
| 1A | A | 470 | 56.7 g/min | 0 | 0 | 100% | 37.8 ml/min | 61.98% | 168 ml/min | 23.05% |
| 1B | A | 470 | 56.7 g/min | 0 | 0 | 100% | 60 ml/min | 50.67% | 168 ml/min | 21.28% |
| 1C | A | 470 | 56.7 g/min | 0 | 0 | 100% | 60 ml/min | 50.67% | 200 ml/min | 19.16% |
| 1D | A | 470 | 40 g/min | 0 | 0 | 100% | 60 ml/min | 42.02% | 168 ml/min | 16.02% |
| 1E | B | 470 | 35 g/min | 0 | 20 ml/min | 63.64% | 100 ml/min | 24.1% | 200 ml/min | 10.6% |
| 1F | B | 250 | 35 g/min | 0 | 20 ml/min | 63.64% | 100 ml/min | 24.1% | 200 ml/min | 10.6% |
| 1G | B | 150 | 35 g/min | 0 | 20 ml/min | 63.64% | 100 ml/min | 24.1% | 200 ml/min | 10.6% |
| 1H | B | 470 | 24.5 g/min | 10.5 g/min | 20 ml/min | 63.64% | 100 ml/min | 24.1% | 200 ml/min | 10.6% |

TABLE 3

Peroxide and p-AV values of the of ETHOCEL ™ Std. 45 canola oil gel samples that are produced by the extrusion process compared with the starting oils and the ETHOCEL ™ Std. 45 canola oil gel samples that are produced by the overhead stirrer process.

| Example or C.E. | Process Conditions* | Process of Preparation | ETHOCEL ™ | Sparge | Antioxidant | Peroxide Value | P-A.V. |
|---|---|---|---|---|---|---|---|
| control | omega 9 canola oil | Not processed | None | | | 2.54 | 2.725 |
| C.E. A | EC45A | Overhead Stirrer | 10.6% ETHOCEL ™ St 45 | None | None | 0.3 | 13.69 |
| 2A | 1E | Extrusion | 10.6% ETHOCEL ™ St 45 | None | None | 1.85 | 5.688 |
| 2B | 1E | Extrusion | 10.6% ETHOCEL ™ St 45 | 30 min N2 | None | 2.3 | 4.088 |
| 2C | 1E | Extrusion | 10.6% ETHOCEL ™ St 45 | None | 0.93 g tocopherol AO/kg oil | 2.34 | 3.422 |
| 2D | 1E | Extrusion | 10.6% ETHOCEL ™ St 45 | 30 min N2 | 0.93 g tocopherol AO/kg oil | 0 | 4.671 |

Some oxidation of the oil and ethylcellulose occurs during processing. The oxidation process can be divided into two phases: in the first phase, fatty acids react with oxygen and generate odorless peroxide compounds, while in the second phase peroxides degrade into various substances that are responsible for rancid odor and smell. The PV test can be used to determine the primary oxidation products while the p-AV test can be used for measuring the secondary products. These two values can be combined to evaluate the oxidation level of samples: with PV oxidative status of the product while with P-AV value the oxidative history of the product can be determined.

As shown in Table 3, prior to processing, both the PV and the p-AV values of the omega 9 canola oil are as low as 2.5 and 2.7. These low values suggest the oxidation history of the canola oil is low. When the traditional overhead stirring process is used to produce gel samples in Comparative Experiment A, the PV is 0.3 while the p-AV value increased to be 13.69. The high p-AV value suggests that the samples have high level of oxidative history due to the oxidation that occurs during the traditional process. However, when the extrusion process is used to produce gel samples the p-AV values are below 5.7 while the PV also stays below 2.5. Thus, by using the extrusion process the p-AV value of the samples are decreased by more than 58% compare to the samples prepared with the traditional process. Addition of antioxidant during extrusion or sparging the oil with nitrogen prior to extrusion further decreases the p-AV level of the resulting samples by 75% and 70%, respectively, compared to the samples prepared with the traditional process of Comparative Experiment A.

EXAMPLE 3

Processing Effect on the Oxidation Levels of the ETHOCEL™ Std. 45 Sunflower Oil Gel Samples Example 2 is repeated except that canola oil is replaced with sunflower oil. PV and p-AV values of the samples are measured to determine their oxidation levels. The results are summarized in Table 4.

Comparative Experiment B

Processing Effect on the Oxidation Levels of the ETHOCEL™ Std. 45 Sunflower Oil Gel Samples (not an Embodiment of the Invention)

Comparative Experiment A is repeated except that the canola oil is replaced with sunflower oil. The results are summarized in Table 4. The sample labeled 3E is passed through a heat exchanger and is collected in a room temperature glass jar as opposed to being collected in a heated, insulated glass jar. The heat exchanger consists of 19 feet of ½ inch diameter stainless steel tubing exposed to the lab air. The exit temperature from the heat exchanger is <60° C.

TABLE 4

Peroxide and p-AV values of the of ETHOCEL ™ Std. 45 sunflower oil gel samples that are produced by the extrusion process compared with the starting oils and the ETHOCEL ™ Std. 45 sunflower oil gel samples that are produced by the overhead stirrer process.

| Sample ID | Process Conditions* | Process of Preparation | ETHOCEL ™ | Sparge | Antioxidant | Peroxide Value | P-A.V. |
|---|---|---|---|---|---|---|---|
| Control | Sunflower Oil | No processed | None | | | 8.12 | 1.95 |
| C.E. 4 | EC45SOA | Overhead Stirrer | 10.6% ETHOCEL ™ St 45 | None | None | 1.86 | 32.136 |

TABLE 4-continued

Peroxide and p-AV values of the of ETHOCEL ™ Std. 45 sunflower oil gel samples that are produced by the extrusion process compared with the starting oils and the ETHOCEL ™ Std. 45 sunflower oil gel samples that are produced by the overhead stirrer process.

| Sample ID | Process Conditions* | Process of Preparation | ETHOCEL ™ | Sparge | Antioxidant | Peroxide Value | P-A.V. |
|---|---|---|---|---|---|---|---|
| 3A | 1E | Extrusion | 10.6% ETHOCEL ™ St 45 | None | None | 8.12 | 6.975 |
| 3B | 1F | Extrusion | 10.6% ETHOCEL ™ St 45 | None | None | 18.41 | 5.843 |
| 3C | 1G | Extrusion | 10.6% ETHOCEL ™ St 45 | None | None | 13.95 | 7.297 |
| 3D | 1E | Extrusion | 10.6% ETHOCEL ™ St 45 | 30 min N2 | None | 12.73 | 6.231 |
| 3E | 1E (HE) | Extrusion | 10.6% ETHOCEL ™ St 45 | 30 min N2 | None | 4.66 | 4.972 |

HE indicates that the ETHOCEL ™/sunflower oil blend is passed through a heat exchanger before collection as described above.

Unlike the omega 9 canola oil in Example 2, sunflower oil had high PV value of 8.12 and a low p-AV value of 1.95 prior to processing (Table 4). The high PV suggests the sunflower oil is oxidized yet the oxidation is at an early stage. When the traditional overhead stirring process is used to produce the ethylcellulose sunflower oil gel samples the PV is 1.86 while the p-AV value increases to be 32.13.

The high PV suggests the sunflower oil oxidizes to a peroxide which is a precursor for the more oxidized aldehyde and the oxidation in the starting material is at a preliminary stage. When the traditional overhead heating process is used to produce the ethylcellulose sunflower samples, the PV is 1.86 while the p-AV value increases to be 32.13. The extremely high p-AV value suggest that the traditional process converts the peroxides into aldehydes and adds more additional aldehydes. The samples are significantly more oxidized than the starting material.

When the ethylcellulose sunflower oil gels are produced by the extrusion process, even though the PV values reach as high as 18.4, the p-AV values are below 7.3. The high PV values suggest that even the extrusion samples oxidized further during production at high temperature. However, the p-AV values of the gels prepared with extrusion are 77% lower than those prepared with the traditional process. The low level of p-AV values show that by using the extrusion process the oxidation history of the ethylcellulose sunflower oil gel samples are significantly reduced.

The preceding examples show that oleogels can be manufactured by the extrusion process of the invention to give a surprising reduction in the oxidation level of oleogels. By incorporating the oil directly into melted ethylcellulose, or optionally melted ethylcellulose plus melted surfactant, a superior oleogel results.

What is claimed is:

1. A process comprising:
   (a) feeding ethylcellulose to the feed zone of an extruder, the extruder having a plurality of oil feed ports along its length;
   (b) feeding at least one oily feed material selected from triacylglycerol oils and triacylglycerol fats into at least one of the oil feed ports;
   (c) mixing the oily feed material with the ethylcellulose to form a substantially homogeneous mixture;
   (d) cooling the mixture to form an oleogel.
2. The process of claim 1 wherein weight ratio of oily feed material to ethylcellulose is from 99:1 to 75:25.
3. The process of claim 1 wherein the oily feed material is edible.
4. The process of claim 1 wherein the process is continuous.
5. The process of claim 1 wherein the temperature in the melting zone of the extruder is in the range of from 100 to 200° C.
6. The process of claim 1 wherein the oleogel is edible.
7. The process of claim 1 wherein a portion of the total oily feed material is fed into a first oil feed port, and a second portion of the total oily feed material is fed into a second oil feed port that is located downstream from the first feed port.
8. The process of claim 1 wherein the oleogel comprises an antioxidant.
9. The process of claim 1 wherein a first oil feed port for the oily feed material is located at a point on extruder where the ethyl cellulose has at least partially melted.
10. The process of claim 9, wherein the ethyl cellulose has fully melted.
11. The process of claim 1 wherein the process is conducted under an inert atmosphere at the extruder inlet and outlet.
12. The process of claim 1, wherein essentially no oxygen is in the barrel of the extruder.

* * * * *